US011324459B2

(12) United States Patent
Kim

(10) Patent No.: US 11,324,459 B2
(45) Date of Patent: May 10, 2022

(54) METHODS AND SYSTEMS FOR PET DETECTORS

(71) Applicant: GE Precision Healthcare LLC, Milwaukee, WI (US)

(72) Inventor: Changlyong Kim, Brookfield, WI (US)

(73) Assignee: GE Precision Healthcare LLC, Milwaukee, WI (US)

( * ) Notice: Subject to any disclaimer, the term of this patent is extended or adjusted under 35 U.S.C. 154(b) by 358 days.

(21) Appl. No.: 16/590,276

(22) Filed: Oct. 1, 2019

(65) Prior Publication Data

US 2021/0093261 A1   Apr. 1, 2021

(51) Int. Cl.
*A61B 6/03* (2006.01)
*G01T 1/29* (2006.01)
*G01T 1/24* (2006.01)
*A61B 5/055* (2006.01)

(52) U.S. Cl.
CPC .............. *A61B 6/037* (2013.01); *A61B 5/055* (2013.01); *G01T 1/248* (2013.01); *G01T 1/2985* (2013.01)

(58) Field of Classification Search
None
See application file for complete search history.

(56) References Cited

U.S. PATENT DOCUMENTS

| | | | |
|---|---|---|---|
| 9,405,023 B2 | 8/2016 | Guo et al. | |
| 2013/0306876 A1* | 11/2013 | Uchida | G01T 1/2985 250/366 |
| 2015/0001399 A1* | 1/2015 | Fries | G01T 1/161 250/362 |
| 2016/0170045 A1* | 6/2016 | Kim | G01T 1/2985 250/208.1 |
| 2020/0072988 A1* | 3/2020 | Cho | G01T 7/005 |

OTHER PUBLICATIONS

Gundacker, S. et al., "Time resolution deterioration with increasing crystal length in a TOF-PET system," Nuclear Instruments and Methods in Physics Research A, vol. 737, Feb. 2014, Available Online Nov. 16, 2013, 9 pages.
"MPPC module for PET," Hamamatsu Website, Available Online https://www.hamamatsu.com/resources/pdf/ssd/pet_module_kacc0011e. pdf. Available as Early as Jan. 2016, 15 pages.
Kim, C. et al., "Comparison of Timing Resolution between Inter-Crystal Scatter and In-Crystal Events," Proceedings of the 2017 IEEE Nuclear Science Symposium and Medical Imaging Conference (NSS/MIC), Oct. 21, 2017, Atlanta, Georgia, 3 pages.

* cited by examiner

*Primary Examiner* — Hoon K Song
(74) *Attorney, Agent, or Firm* — McCoy Russell LLP

(57) ABSTRACT

Methods and systems are provided for signal processing in a detector assembly of an imaging system. In one embodiment, an imaging system may include a plurality of detector blocks, each detector block including an array of silicon photomultiplier (SiPM) devices divided into at least two regions, with the SiPM devices in the two or more regions transmitting signals to two or more distinct timing pick-off circuits. In this way, a SiPM array may be subdivided into regions with a signal summed from SiPMs of a single region being transmitted to a separate timing pick-off circuit.

20 Claims, 8 Drawing Sheets

METHODS AND SYSTEMS FOR PET DETECTORS

FIELD

Embodiments of the subject matter disclosed herein relate to non-invasive diagnostic imaging, and more particularly, to signal processing in positron emission tomography (PET) detectors.

BACKGROUND

A positron emission tomography (PET) scanner generates images that represent the distribution of positron-emitting nuclides within the body of a patient. When a positron interacts with an electron by annihilation, the entire mass of a positron-electron pair is converted into two photons (also referred to as events). The photons are emitted in opposite directions along a line of response (LOR). The annihilation photons are detected by detectors that are placed on both sides of the LOR, in a configuration such as a detector ring. In a time of flight (TOF) PET, in addition to measurement of the distance and attenuation of photons, an actual time difference between the detection of photons released during coincident events is measured to more accurately identify the distance from the annihilation event to the detector. The detectors convert the incident photons into useful electrical signals that can be used for image formation. An image thus generated based on the acquired image data includes the annihilation photon detection information.

Modern PET scanners include detectors such as silicon photomultiplier (SiPM) devices, wherein the detectors are typically tuned such that data collection is normalized for the energy event that is being detected. A TOF PET detector including analog application specific integrated chips (ASICs) is desired to demonstrate a coincidence timing resolution (CTR) of lower than 200 ps. In one example, the ASICs may include one to one coupling between a single crystal and a SiPM device (also referred to herein as a SiPM). In order to account for Compton scattering between crystals in the detector, input signals from an array of SiPMs may be consolidated into one timing channel. The response of photonic detectors in the absence of light is termed dark count. In a SiPM, thermionic emission of electrons is a major source of dark counts. During consolidation of input signals from an array of SiPMs, the dark count from the SiPMs s are also summed. In order to maintain the CTR within a range, it is desirable to reduce the effect of dark count on the CTR.

BRIEF DESCRIPTION

In one embodiment, an imaging system comprises one or more detector blocks, each detector block including an array of silicon photomultiplier (SiPM) devices divided into two or more regions, with the SiPM devices in the two or more regions transmitting signals to two or more distinct timing pick-off circuits. In this way, by dividing a SiPM array into regions with each region corresponding to a separate timing pick-off circuit, the detrimental effect of dark counts on a single timing pick-off circuit may be reduced.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present invention will be better understood from reading the following description of non-limiting embodiments, with reference to the attached drawings, wherein below.

DETAILED DESCRIPTION

Figure 2:
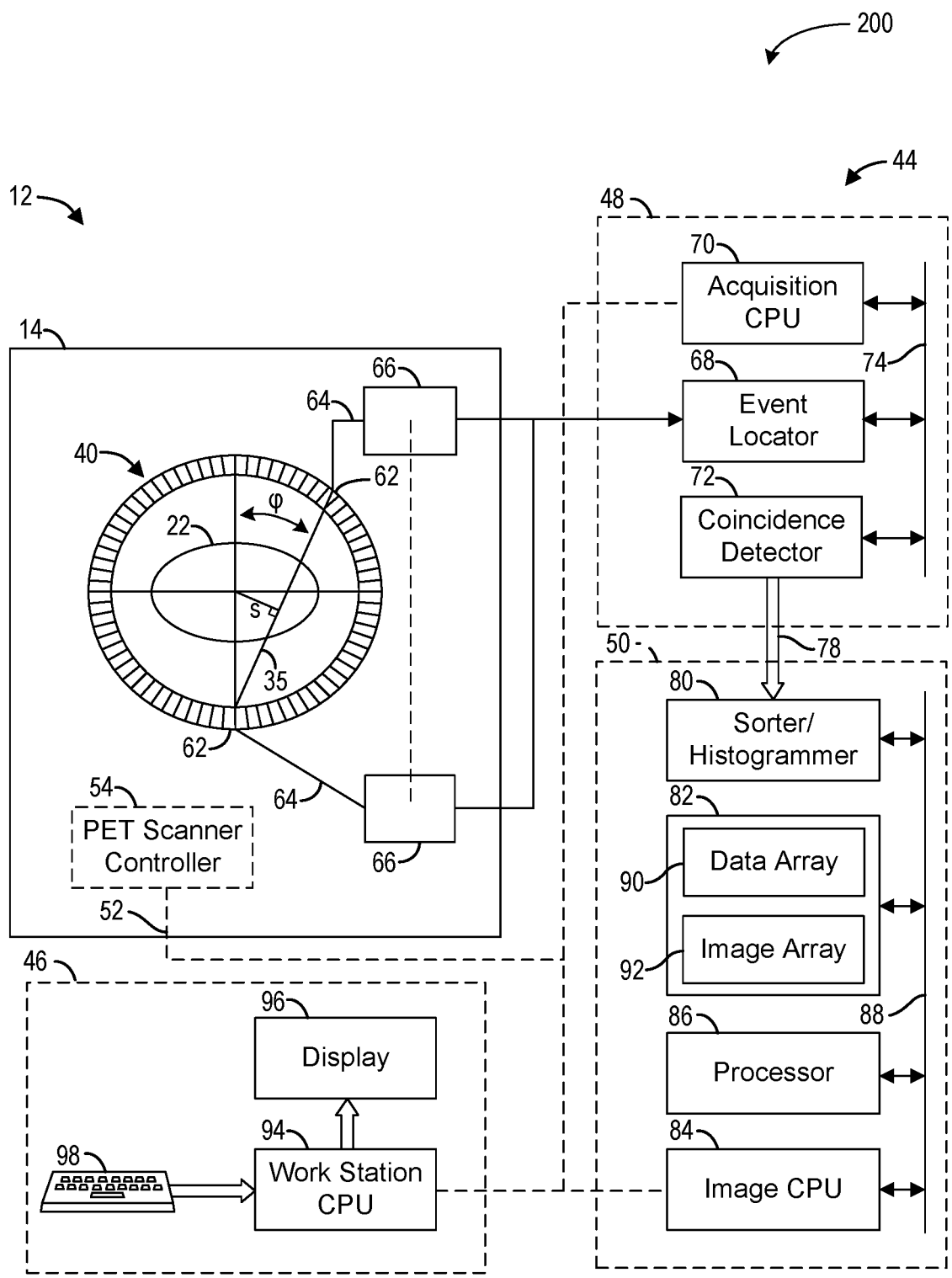
FIG. 2 is a block schematic diagram of an exemplary imaging system with a detector, according to an embodiment of the invention.
Figure 3:
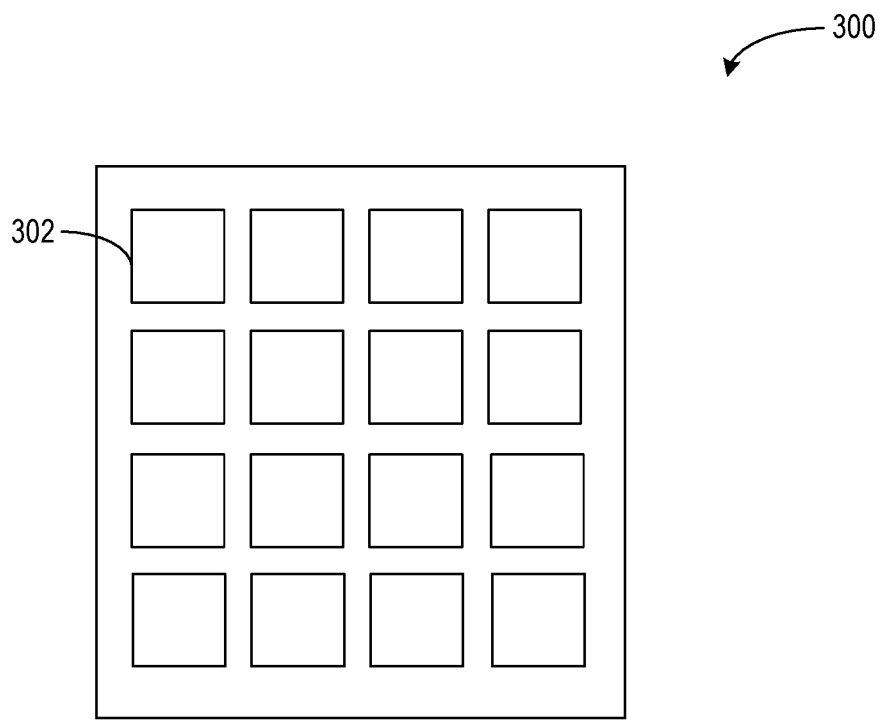
FIG. 3 is a schematic block diagram of a silicon photo-multiplier (SiPM) array, according to an embodiment of the invention.
Figure 4:
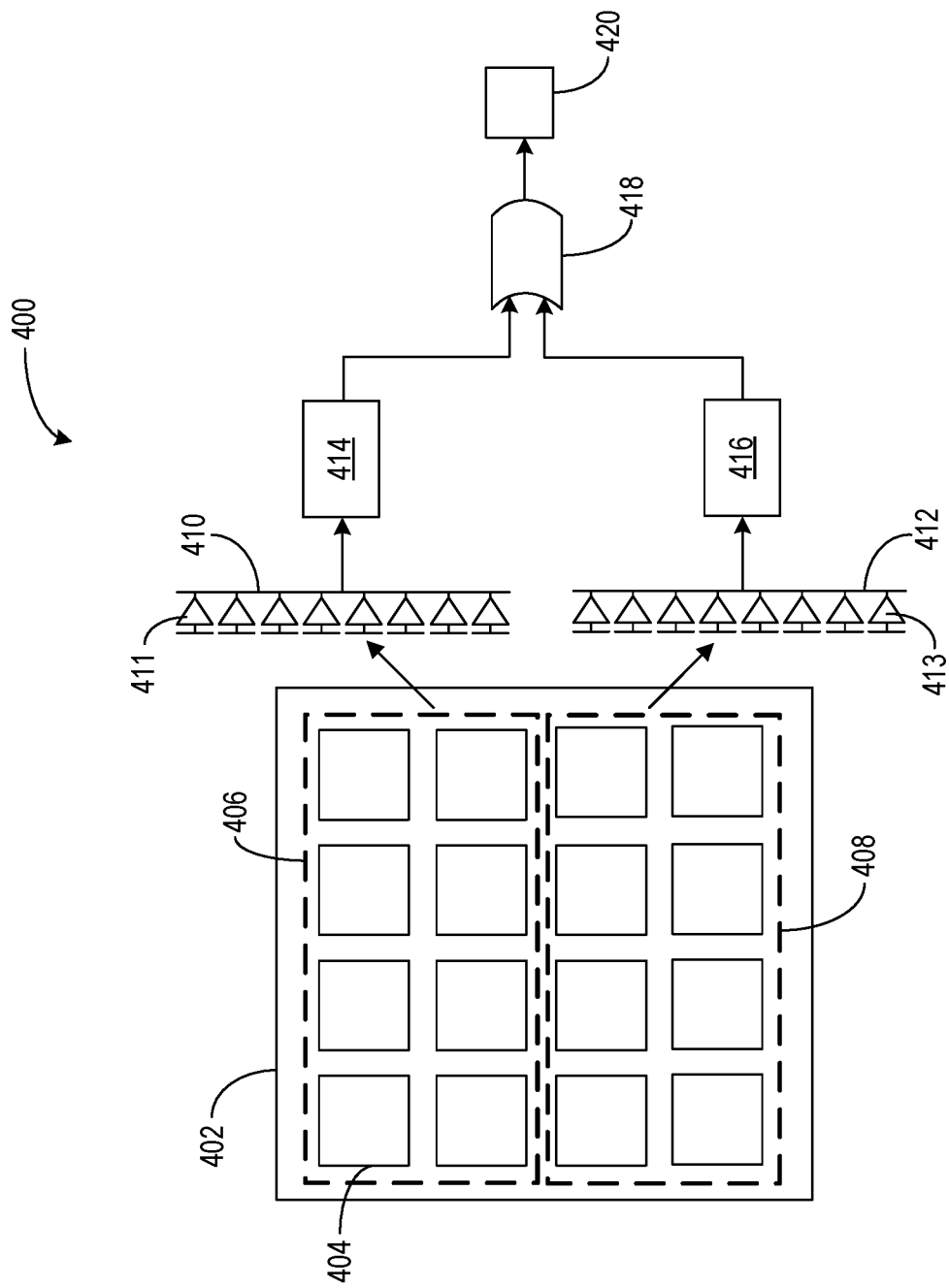
FIG. 4 shows a first example of dividing a SiPM array into multiple regions, with each region corresponding to a separate timing pick-off circuit.
Figure 5:
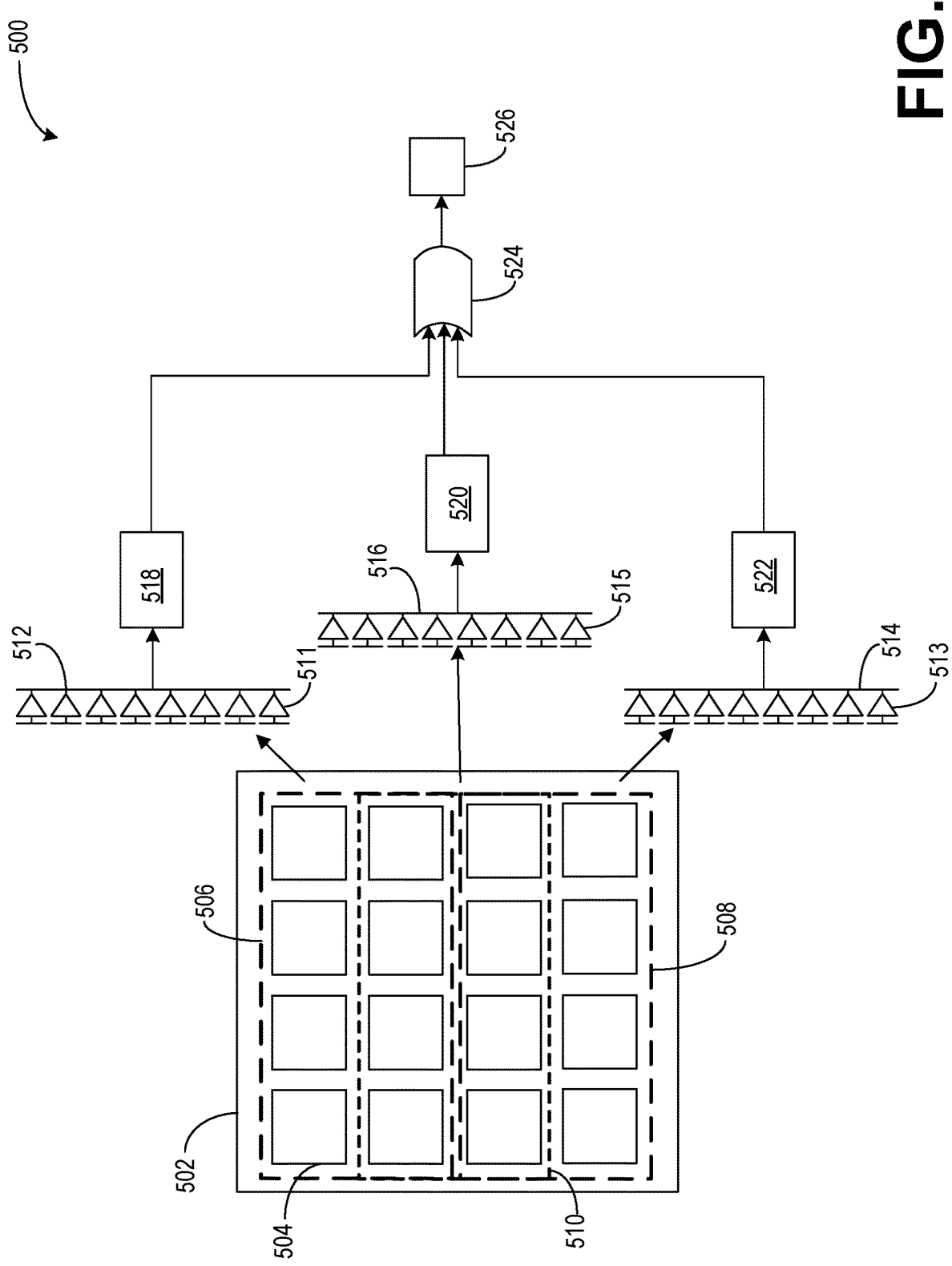
FIG. 5 shows a second example of dividing a SiPM array into multiple overlapping regions, with each region corresponding to a separate timing pick-off circuit.
Figure 6:
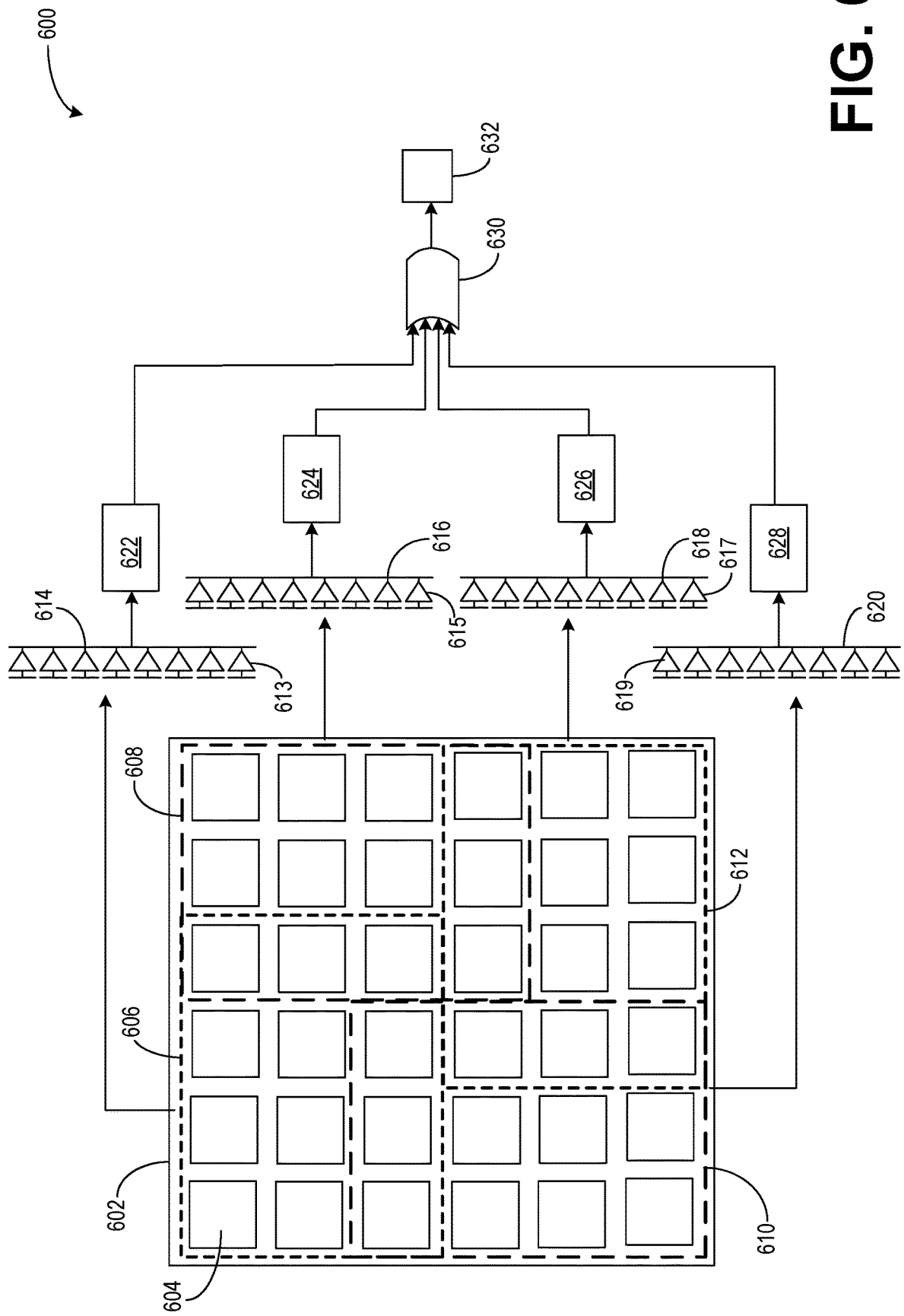
FIG. 6 shows a third example of dividing a SiPM array into multiple overlapping regions with each region corresponding to a separate timing pick-off circuit.
Figure 7:
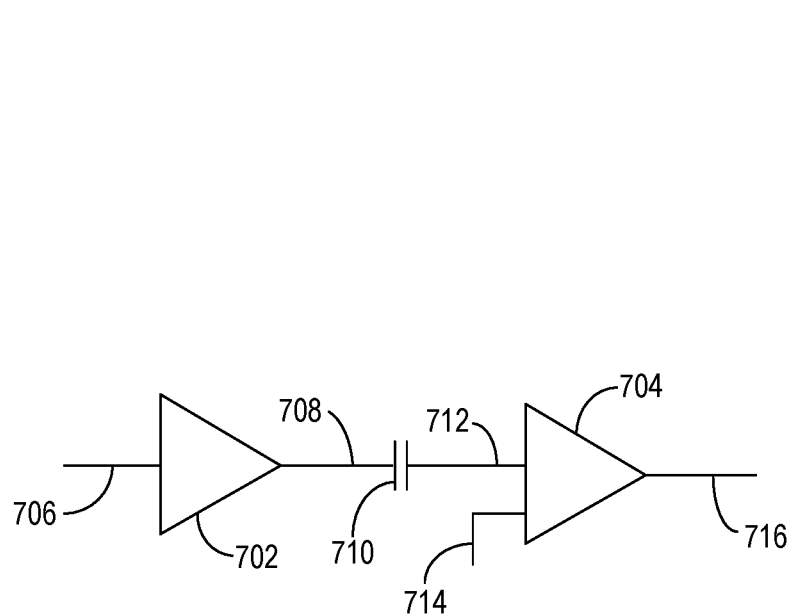
FIG. 7 shows a schematic diagram of a timing pick-off circuit.
Figure 8:
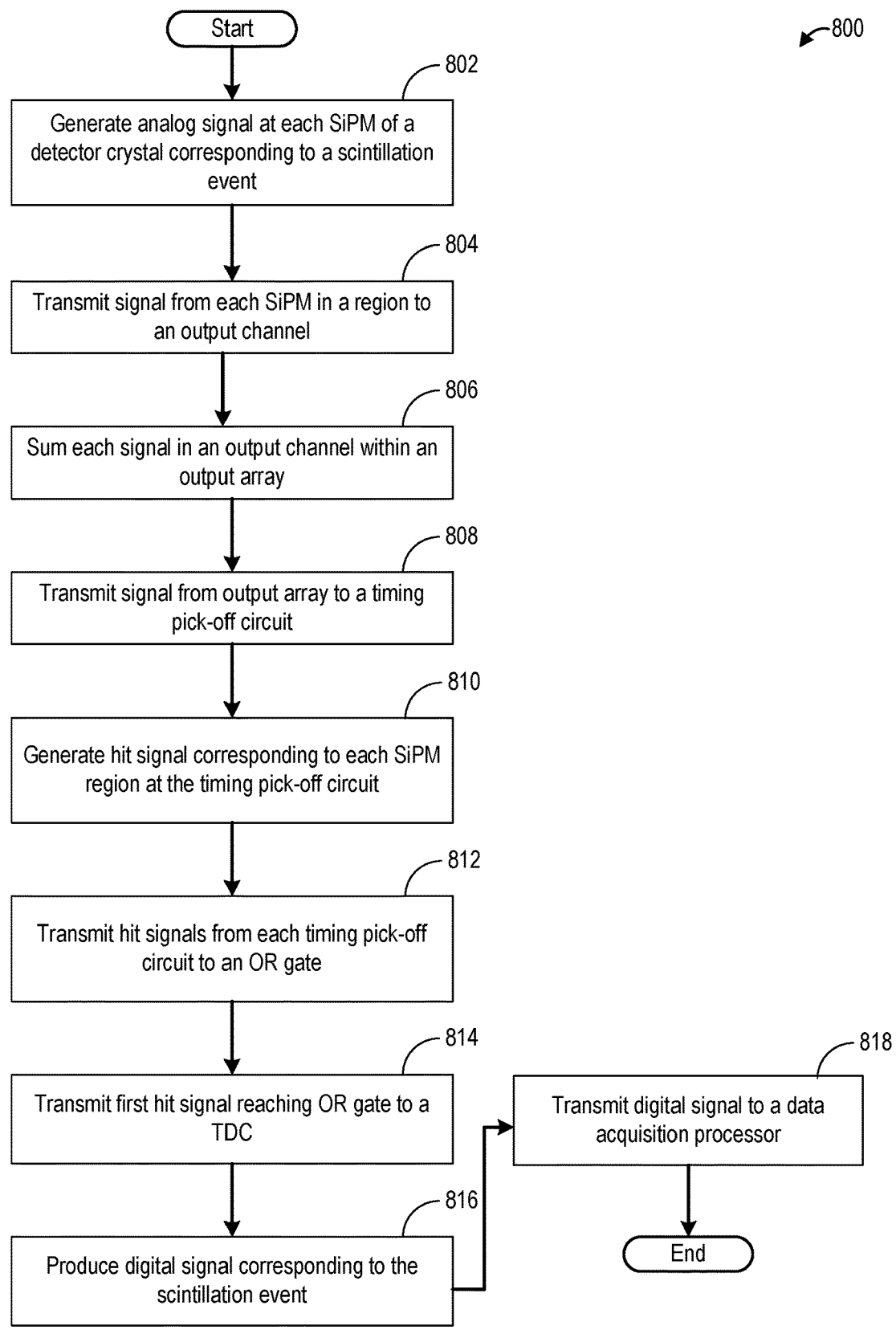
FIG. 8 is a high-level flowchart illustrating an example method for processing signal from a SiPM array.

The following description relates to various embodiments of medical imaging systems. In particular, methods and systems are provided for processing signal from a silicon photomultiplier (SiPM) array of a detector. An example of a positron emission tomography (PET) imaging system including a detector that may be used to detect energy events in accordance with the present techniques is provided in FIGS. 1-2. An example SiPM array constituting a detector block is shown in FIG. 3. The SiPM array may be divided into multiple regions, with each region corresponding to a separate timing pick-off circuit. FIGS. 4-6 show examples of a SiPM array divided into regions. An example timing pick-off circuit corresponding to a single region of a SiPM array is shown in FIG. 7. FIG. 8 shows an example method for processing signal from a SiPM array.

Though a PET imaging system is described by way of example, it should be understood that the present techniques may also be useful when applied to images acquired using other imaging modalities, such as CT, tomosynthesis, MM, C-arm angiography, and so forth. The present discussion of a PET imaging modality is provided merely as an example of one suitable imaging modality.

As used herein, the phrase "reconstructing an image" is not intended to exclude embodiments of the present invention in which data representing an image is generated but a viewable image is not. Therefore, as used herein the term "image" broadly refers to both viewable images and data representing a viewable image. However, many embodiments generate, or are configured to generate, at least one viewable image.

In one example, analog application specific integrated chips (ASICs) may include one-to-one coupling between a single detector crystal and a SiPM causing each SiPM to readout individually. However, in order to account for Compton scattering amongst crystals and to reduce the cost of the associated electronics (Time-to-Digital converter (TDC), Analog-to-Digital converter (ADC), FPGAs, etc.), input signals from an array of SiPMs may be consolidated into one timing channel. The response of photonic detectors in the absence of light is known as dark count. In a SiPM, thermionic emission of electrons is a major source of dark counts. During consolidation of input signals from an array of SiPMs, along with the actual signal, the dark counts from the SiPMs are also summed. In order to maintain the CTR within a range, it is desirable to reduce the effect of dark count on the CTR.

In case of a one-to-one coupling between a single crystal and a SiPM, dark count (such as caused by thermionic emission of electrons) of a single SiPM may be added to the gamma ray signal regenerated from the SiPM. However, due to Compton scattering, certain gamma rays may interact with a plurality of detector crystals. As an example, when a gamma ray is scattered, the energy of the gamma ray may be split over two or more crystals which reduces the size of the signal going into the comparator and degrades the coincidence timing resolution (CTR) of Compton scattered gamma rays. In order to overcome the effect of Compton scattering, instead of channeling signal from a single SiPM to a single timing pick-off circuit, signal from an array of SiPMs may be summed and channeled to the single timing pick-off circuit. With an increase in the number of SiPMs in a detector block, the CTR may be improved while the number of detector blocks may be reduced for the system, thereby reducing the cost of the associated electronic components.

However, the dark counts from each SiPM in an array may be summed up in the input signal to the timing pick-off circuit which may increase the noise associated with the signal. The increased dark counts may degrade the CTR. The dark count effect on the CTR increases as a number of SiPMs in a detector block increase. In order to limit the influence of dark counts on the CTR, a system is proposed to limit the number of SiPM inputs to one timing pick-off circuit by adding additional timing pick-off circuits without a change in the size of the detector block and the cost of the associated electronics low As an example, a SiPM array may be divided into two or more regions with signal from each region used as an input signal for a single timing pick-off circuit. Dark counts from SiPMs in a single region may be summed in the input signal. By summing dark counts from a lower number of SiPMs, the detrimental effect of dark counts on the input signal may be reduced. In this way, the detrimental effects of Compton scattering may be reduced by incorporating an array of SiPMs and the detrimental effects of dark count summation may be lowered by dividing the array of SiPMs into multiple regions with each region corresponding to a separate timing pick-off circuit.

Figure 1:
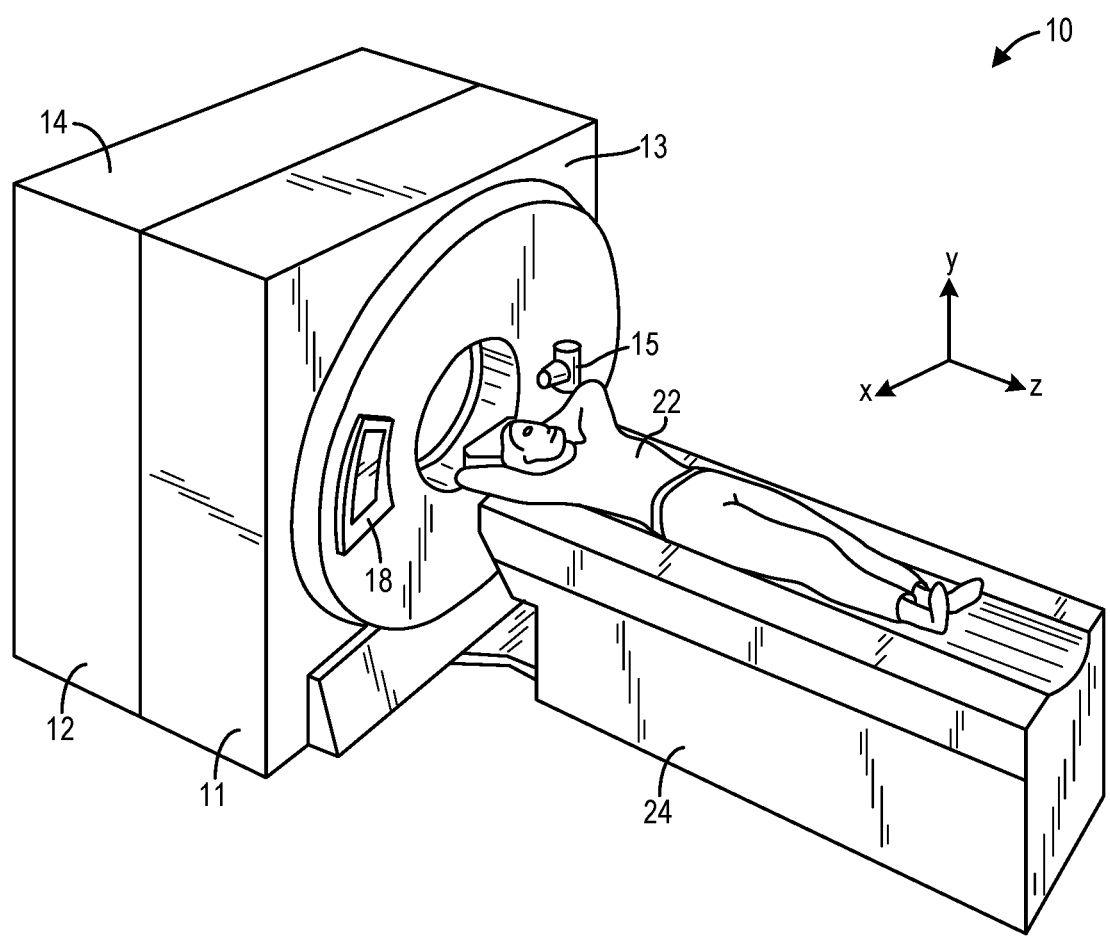
FIG. 1 is a pictorial view of an exemplary multi-modality imaging system according to an embodiment of the invention.

If each divided region in a SiPM array is small, a non-negligible amount of Compton events may be present which may degrade the CTR. To improve the CTR caused by inter-region Compton scatter, an overlap region may be created by duplicating the SiPM signal in the overlap region, which may capture the energy of inter-region Compton scatter fully, and adding one or more timing pick-off circuits. Signals from the plurality of timing pick-off circuits may be directed to an OR gate and the timing signal which reaches the OR gate first may be transmitted to a time-to-digital converter. By keeping the signal delay lines same from SiPMs to a timing pick-off circuit and then to an OR gate, the largest signal among the signals of the regions reaches the OR gate first Various embodiments of the invention provide a multi-modality imaging system 10 as shown in FIGS. 1 and 2. Multi-modality imaging system 10 may be any type of imaging system, for example, different types of medical imaging systems, such as a Positron Emission Tomography (PET), a Single Photon Emission Computed Tomography (SPECT), a Computed Tomography (CT, an ultrasound system, Magnetic Resonance Imaging (MM), or any other system capable of generating tomographic images. The various embodiments are not limited to multi-modality medical imaging systems, but may be used on a single modality medical imaging system such as a stand-alone PET imaging system or a stand-alone SPECT imaging system, for example. Moreover, the various embodiments are not limited to medical imaging systems for imaging human subjects, but may include veterinary or non-medical systems for imaging non-human objects.

Referring to FIG. 1, the multi-modality imaging system 10 includes a first modality unit 11 and a second modality unit 12. The two modality units enable the multi-modality imaging system 10 to scan an object or patient in a second modality using the second modality unit 12. The multi-modality imaging system 10 allows for multiple scans in different modalities to facilitate an increased diagnostic capability over single modality systems. In one embodiment, multi-modality imaging system 10 is a Computed Tomography/Positron Emission Tomography (CT/PET) imaging system 10, e.g., the first modality 11 is a CT imaging system 11 and the second modality 12 is a PET imaging system 12. The CT/PET system 10 is shown as including a gantry 13 representative of a CT imaging system and a gantry 14 that is associated with a PET imaging system. As discussed above, modalities other than CT and PET may be employed with the multi-modality imaging system 10.

The gantry 13 includes an x-ray source 15 that projects a beam of x-rays toward a detector array 18 on the opposite side of the gantry 13. Detector array 18 is formed by a plurality of detector rows (not shown) including a plurality of detector elements which together sense the projected x-rays that pass through a medical patient 22. Each detector element produces an electrical signal that represents the intensity of an impinging x-ray beam and hence allows estimation of the attenuation of the beam as it passes through the patient 22. During a scan to acquire x-ray projection data, gantry 13 and the components mounted thereon rotate about a center of rotation.

FIG. 2 is a block schematic diagram 200 of the PET imaging system 12 illustrated in FIG. 1 in accordance with an embodiment of the present invention. The PET imaging system 12 includes a detector ring assembly 40 including a plurality of detector blocks. The PET imaging system 12 also includes a controller or processor 44, to control normalization, image reconstruction processes and perform calibration. Controller 44 is coupled to an operator workstation 46. Controller 44 includes a data acquisition processor 48 and an image reconstruction processor 50, which are interconnected via a communication link 52. PET imaging system 12 acquires scan data and transmits the data to data acquisition processor 48. The scanning operation is controlled from the operator workstation 46. The data acquired by the data acquisition processor 48 is reconstructed using the image reconstruction processor 50.

The detector ring assembly 40 includes a central opening, in which an object or patient, such as patient 22 may be positioned using, for example, a motorized table 24 (shown in FIG. 1). The motorized table 24 is aligned with the central axis of detector ring assembly 40. This motorized table 24 moves the patient 22 into the central opening of detector ring assembly 40 in response to one or more commands received from the operator workstation 46. A PET scanner controller 54, also referred to as the PET gantry controller, is provided (e.g., mounted) within PET system 12. The PET scanner controller 54 responds to the commands received from the operator workstation 46 through the communication link 52. Therefore, the scanning operation is controlled from the operator workstation 46 through PET scanner controller 54.

During operation, when a photon collides with a crystal in a detector block 62 on a detector ring 40, it produces a scintillation event on the crystal. Each photomultiplier tube or photosensor produces an analog signal that is transmitted on communication line 64 when a scintillation event occurs. A set of acquisition circuits 66 is provided to receive these analog signals. Acquisition circuits 66 produce digital signals indicating the three-dimensional (3D) location and total energy of the event. The acquisition circuits 66 also produce an event detection pulse, which indicates the time or moment the scintillation event occurred. These digital signals are transmitted through a communication link, for example, a cable, to an event locator circuit 68 in the data acquisition processor 48.

The data acquisition processor 48 includes the event locator circuit 68, an acquisition CPU 70, and a coincidence detector 72. The data acquisition processor 48 periodically samples the signals produced by the acquisition circuits 66. The acquisition CPU 70 controls communications on a back-plane bus 74 and on the communication link 52. The event locator circuit 68 processes the information regarding each valid event and provides a set of digital numbers or values indicative of the detected event. For example, this information indicates when the event took place and the position of the scintillation crystal in a detector block 62 that detected the event. An event data packet is communicated to the coincidence detector 72 through the back-plane bus 74. The coincidence detector 72 receives the event data packets from the event locator circuit 68 and determines if any two of the detected events are in coincidence. Coincidence is determined by a number of factors. First, the time markers in each event data packet must be within a predetermined time period, for example, 4.5 nanoseconds, of each other. Second, the line-of-response (LOR) formed by a straight line joining the two detectors that detect the coincidence event should pass through the field of view in the PET imaging system 12. Events that cannot be paired are discarded. Coincident event pairs are located and recorded as a coincidence data packet that is communicated through a physical communication link 78 to a sorter/histogrammer 80 in the image reconstruction processor 50.

The image reconstruction processor 50 includes the sorter/histogrammer 80. During operation, sorter/histogrammer 80 generates a data structure known as a histogram. A histogram includes a large number of cells, where each cell corresponds to a unique pair of detector crystals in the PET scanner. Because a PET scanner typically includes thousands of detector crystals, the histogram typically includes millions of cells. Each cell of the histogram also stores a count value representing the number of coincidence events detected by the pair of detector crystals for that cell during the scan. At the end of the scan, the data in the histogram is used to reconstruct an image of the patient. The completed histogram containing all the data from the scan is commonly referred to as a "result histogram." The term "histogrammer" generally refers to the components of the scanner, e.g., processor and memory, which carry out the function of creating the histogram.

The image reconstruction processor 50 also includes a memory module 82, an image CPU 84, an array processor 86, and a communication bus 88. During operation, the sorter/histogrammer 80 counts all events occurring along each projection ray and organizes the events into 3D data. This 3D data, or sinogram, is organized in one exemplary embodiment as a data array 90. Data array 90 is stored in the memory module 82. The communication bus 88 is linked to the communication link 52 through the image CPU 84. The image CPU 84 controls communication through communication bus 88. The array processor 86 is also connected to the communication bus 88. The array processor 86 receives data array 90 as an input and reconstructs images in the form of image array 92. Resulting image arrays 92 are then stored in memory module 82.

The images stored in the image array 92 are communicated by the image CPU 84 to the operator workstation 46. The operator workstation 46 includes a CPU 94, a display 96, and an input device 98. The CPU 94 connects to communication link 52 and receives inputs, e.g., user commands, from the input device 98. The input device 98 may be, for example, a keyboard, mouse, a touch-screen panel, and/or a voice recognition system, and so on. Through input device 98 and associated control panel switches, the operator can control the operation of the PET imaging system 12 and the positioning of the patient 22 for a scan. Similarly, the operator can control the display of the resulting image on the display 96 and can perform image-enhancement functions using programs executed by the workstation CPU 94.

The detector ring assembly 40 includes a plurality of detector units. The detector unit may include a plurality of detectors, light guides, scintillation crystals and analog application specific integrated chips (ASICs). For example, the detector unit may include twelve silicon photomultipliers (SiPM) devices, four light guides, 144 scintillation crystals, and two analog ASICs.

As an example, a detector block 62 may include an array of scintillation crystals and an array of SiPM devices. The SiPM devices may be divided into two or more regions with the SiPMs devices in the two or more regions transmitting signals to two or more distinct timing pick-off circuits. Each of the two or more regions in the array of SiPM devices may include at least one SiPM device. In one example, the at least one SiPM device may be included in one of the two or more regions, each of the two or more regions mutually exclusive. In another example, the at least one SiPM device may be included in two of the two or more regions, the two of the two or more regions overlapping each other. Each region of the two or more regions may transmit signal to one of the two or more distinct timing pick-off circuits via an output array. The output array may include a number of output channels with the number of output channels in the output array being equal to a number of SiPM devices in a region coupled to the output array with each SiPM device mapped to an output channel in the output array. An output channel may receive an analog signal from a SiPM device and each analog signal from each output channel in the output array may be summed to generate an input signal for a timing pick-off circuit coupled to the output array, the analog signal generated by collection of scintillation photons with the SiPM device.

Each timing pick-off circuit of the two or more distinct timing pick-off circuits may include a summing amplifier, a capacitor, and a comparator connected in series, each timing pick-off circuit comparing the input signal to a threshold signal and in response to the input signal being higher than the threshold signal, generating a square pulse signal. Each timing pick-off circuit output may be coupled to a logic circuit such as an OR gate. The logic circuit may receive square pulse signals from the two or more timing pick-off circuits and transmit a square pulse signal reaching the logic circuit first to a time to digital converter (TDC). The TDC may be part of acquisition circuits 66 of the PET imaging system.

An example detector block with a plurality of SiPMs is shown in FIG. 3 arranges in an array. As such, each SiPM may further include a plurality of pixels (6, for example). An example where the detector unit 300 includes sixteen SiPMs is shown in FIG. 3. In such an example, each SiPM 302 includes plurality of pixels. For example, the SiPM 302 may include 6 pixels. As such the detector unit 300 then includes a total of 96 pixels (determined by 6×16). The signal output from each of the SiPMs may be summed and the summed signal may be used as an input signal for a timing pick-off circuit. However, with summing the signal outputs from all SiPMs in an array, the collective dark counts may be amplified, thereby affecting the signal quality. As shown in FIGS. 4-7, a SiPM array may be divided into multiple regions with each region corresponding to a timing pick-off circuit.

FIG. 4 shows a first example 400 of a detector block 402 including sixteen individual SiPMs 404 forming an array. The SiPMs 404 may be arranged in a 4×4 matrix. The sixteen SiPMs may be divided into two separate regions with the top eight SiPMs forming a first region 406 and the lower eight SiPMs forming a second region 408. The division of regions as shown here is an example configuration and any number of SiPMs may be configured as a region. In one example, the first region may include 7 SiPMs while the second region may include the remaining 9 SiPMs.

The SiPMs from the first region 406 may correspond to a first output array 410. The first output array 410 may include eight individual output channels 411 (also referred herein as front-end amplifier) with each output channel 411 directly receiving signal from one SiPM. Each output channel 411 may be mapped to a single SiPM in the first region 406. Similarly, the SiPMs from the second region 408 may correspond to a second output array 412. The second output array 412 may include eight individual output channels 413 with each output channel 413 directly receiving signal from one SiPM. Each output channel 413 may be mapped to a single SiPM in the second region 408.

The first output array 410 may receive individual signals from eight SiPMs and sum the signal to form a single input signal for a first timing pick-off circuit 414. The second output array 412 may receive individual signals from eight SiPMs and sum the signal to form a single input signal for a second timing pick-off circuit 416. By channeling signal from a plurality of SiPMs to a single timing pick-off circuit, the detrimental effect of Compton scattering on signal quality may be reduced. By dividing the SiPMs into two groups, the accumulated dark count in the input signals for the first timing pick-off circuit 414 and the second timing pick-off circuit 416 may each be reduced relative to an accumulated dark count in an input signal obtained from summing all sixteen SiPMs in the detector unit. In this way, by including an array of SiPMs in a detector block and separately processing signals from regions in the array, detrimental effects of Compton scattering and dark count accumulation may be reduced.

An example timing pick-off circuit 700 is shown in FIG. 7. The timing pick-off circuit 700 may be the first timing pick-off circuit 414 or second timing pick-off circuit 416 in FIG. 4. The timing pick-off circuit includes a summing amplifier 702, a capacitor 710, and a comparator 704 connected in series.

An output array may sum the signals received from individual SiPMs and generate an input signal 706 for the summing amplifier 702. At the summing amplifier 702, all input signals are summed and may be amplified with a low noise and high bandwidth amplifier. The output signal 708 from the summing amplifier 702 may pass through the capacitor 710 wherein only the high frequency component of the signal passes through to improve CTR while a low frequency electronic noise and a low frequency component of the summed signal 708 gets filtered out. After passing through the capacitor 710, the signal 712 passes through the comparator 704. At the comparator, the signal 712 is compared to a threshold signal 714 and if the signal 712 is higher than the threshold signal 714, a square pulse may be generated. The square pulse may be termed as a hit signal generated from the timing pick-off circuit 700.

Returning to FIG. 4, the respective hit signals generated from the first timing pick-off circuit 414 and the second timing pick-off circuit 416 may be transmitted to an OR gate 418. At the OR gate, the first arriving hit signal between two binary signals (hit signals) generates its output that gets transmitted to TDC 420. As such, when the signal trace lengths are kept same, the largest signal, among the signals of 706, reaching the timing pick-off comparator 704 may generate the hit signal first and reach the OR gate 418 first.

The signal from the OR gate 418 may then be transmitted to a time to digital converter (TDC) 420. The TDC 420 may recognize events in the form of signals reaching the TDC from the OR gate 418 and provide a digital representation of the time they occurred. For example, a TDC might output the time of arrival for each incoming signal. In one example, each of the first timing pick-off circuit 414, the second timing pick-off circuit 416, the OR gate 418, and the TDC 420 may be part of acquisition circuits (such as acquisition circuits 66 in FIG. 2) of the PET imaging system.

Compton scattering may take place between the two regions in the SiPM array in the detector block 402. In order to further reduce the effect of inter-region Compton scattering and improve the CTR, an overlap region may be included by duplicating the SiPM signal in the overlap region, which may capture the energy of inter-region Compton scatters fully, and adding one or more timing pick-off circuits.

FIG. 5 shows a second example 500 of a detector unit 502 including sixteen individual SiPMs 504 divided into overlapping regions corresponding to separate timing pick-off circuits. The SiPMs may be arranged in a 4×4 matrix. The sixteen SiPMs may be divided into three regions with the top eight SiPMs forming a first region 506, the lower eight SiPMs forming a second region 508, and the middle eight SiPMs forming a third region 510. Four SiPMs in the third region 510 is shared with the first region 506 while the four other SiPMs in the third region 510 is shared with the second region 508. In this way, the third region 510 overlaps with each of the first region 506 and the second region 508. The division of regions as shown here is an example configuration and any number of SiPMs may be configured as a region.

The SiPMs from the first region 606 may correspond to a first output array 512. The first output array 512 may include eight individual output channels 511 with each output channel 511 directly receiving signal from one SiPM. Each output channel 511 may be mapped to a single SiPM in the first region 506. Similarly, the SiPMs from the second region 508 may correspond to a second output array 514. The second output array 514 may include eight individual output channels 513 with each output channel 513 directly receiving signal from one SiPM. Each output channel 513 may be mapped to a single SiPM in the second region 508. The third output array 516 may include eight individual output channels 515 with each output channel 515 directly receiving signal from one SiPM. Each output channel 515 may be mapped to a single SiPM in the third region 510. In this way, each SiPM in the third region 510 provides output to two output channels.

In one example, a SiPM in the third region 510 provides outputs to each of an output channel 511 in the first output array 512 and an output channel 515 in the third output array 516. In another example, a SiPM in the third region 510 provide outputs to each of an output channel 513 in the second output array 514 and an output channel 515 in the third output array 516. In this way, by duplicating signals from a plurality of SiPMs, the detrimental effect of inter-region Compton scattering may be reduced and signal to noise ratio may be improved. The duplication of a signal from a SiPM may be accomplished at the output channels.

The first output array 512 may receive individual signals from eight SiPMs and sum the signal to form a single input signal for a first timing pick-off circuit 518. The second output array 514 may receive individual signals from eight SiPMs and sum the signal to form a single input signal for a second timing pick-off circuit 522. The third output array 516 may receive individual signals from eight SiPMs and sum the signal to form a single input signal for a third timing pick-off circuit 520.

The respective hit signals generated from the first timing pick-off circuit 518, the second timing pick-off circuit 522, and the third timing pick-off circuit 520 may be transmitted to an OR gate 524. The signal trace lengths from the SiPMs 504 to the OR gate 524 may be matched among the sub groups (such as the SiPMs in the first, second, and third regions). At the OR gate, the first arriving hit signal between three signals (hit signals) may generate an output pulse to be transmitted to a TDC. Whichever hit signal (from one of the first timing pick-off circuit 518, the second timing pick-off circuit 522, and the third timing pick-off circuit 520) reaches the OR gate first will be transmitted to a time to digital converter (TDC) 526. The TDC 526 may recognize events in the form of signals reaching the TDC from the OR gate 526 and provide a digital representation of the time they occurred.

FIG. 6 shows a third example 600 of a detector block 602 including 36 individual SiPMs 604 divided into overlapping regions corresponding to separate timing pick-off circuits. The SiPMs may be arranged in a 6×6 matrix. As the size of a detector block gets larger with more SiPMs, the cost of associated electronics may be reduced. However, the total dark count may increase with more SiPMs. The 36 SiPMs may be divided into four regions to reduce the effect of dark counts. Twelve SiPMs in a top left corner of the 6×6 array may form a first region 606, twelve SiPMs in a top right corner of the 6×6 array may form a second region 608, twelve SiPMs in a lower left corner of the 6×6 array may form a third region 610, and twelve SiPMs in a lower right corner of the 6×6 array may form a fourth region 612.

The first region 606 overlaps with each of the second region 608 and the third region 610 with three shared SiPMs between the first and the second regions and another three shared SiPMs between the first and the third regions. The second region 608 overlaps with each of the first region 606 and the fourth region 612 with three shared SiPMs between the first and the second regions and another three shared SiPMs between the second and the fourth regions. The third region 610 overlaps with each of the first region 606 and the fourth region 612 with three shared SiPMs between the third and the first regions and another three shared SiPMs between the third and the fourth regions. The fourth region 612 overlaps with each of the second region 608 and the third region 610 with three shared SiPMs between the fourth and the second regions and another three shared SiPMs between the fourth and the third regions.

All SiPMs in the third region 510 in FIG. 5 are overlapped with the neighboring regions. In FIG. 6, only a fraction of SiPMs in a region are overlapped with the neighboring regions to minimize the number of output channels 614, 616, 618, 620, and timing pick-off circuits 622, 624, 626, 628. The minimization of the necessary electronics may reduce both the power consumption of the ASIC and the electronic noise sources. The regions in FIG. 6 is an example embodiment and the size of regions may be adjusted based on the amount of dark count from each SiPM, the size of SiPMs, the targeted size of a block detector, and the desired of the CTR level.

The division of regions as shown here is an example configuration and any number of SiPMs may be configured as overlapping regions.

The SiPMs from the first region 606 may correspond to a first output array 614. The first output array 614 may include eight individual output channels 613 with each output channel 613 directly receiving signal from one SiPM. Each output channel 613 may be mapped to a single SiPM in the first region 606. Similarly, the SiPMs from the second region 608 may correspond to a second output array 616. The second output array 616 may include eight individual output channels 615 with each output channel 615 directly receiving signal from one SiPM. Each output channel 615 may be mapped to a single SiPM in the second region 608. The third output array 620 may include eight individual output channels 619 with each output channel 619 directly receiving signal from one SiPM. Each output channel 619 may be mapped to a single SiPM in the third region 610. The fourth output array 618 may include eight individual output channels 617 with each output channel 617 directly receiving signal from one SiPM. Each output channel 617 may be mapped to a single SiPM in the fourth region 612.

In one example, a SiPM in the first region 606 may provide outputs to each of an output channel 613 in the first output array 614 and an output channel 615 in the second output array 616. In another example, another SiPM in the first region 606 may provide outputs to each of an output channel 613 in the first output array 614 and an output channel 619 in the third output array 620. In this way, by duplicating signals from a plurality of SiPMs, the detrimental effect of inter-region Compton scattering may be reduced and signal to noise ratio may be improved.

The first output array 614 may receive individual signals from eight SiPMs and sum the signal to form a single input signal for a first timing pick-off circuit 622. The second output array 616 may receive individual signals from eight SiPMs and sum the signal to form a single input signal for a second timing pick-off circuit 624. The third output array 620 may receive individual signals from eight SiPMs and sum the signal to form a single input signal for a third timing pick-off circuit 628. The fourth output array 618 may receive individual signals from eight SiPMs and sum the signal to form a single input signal for a fourth timing pick-off circuit 626.

The respective hit signals generated from each of the first timing pick-off circuit 622, the second timing pick-off circuit 624, the third timing pick-off circuit 628, and the fourth timing time-off circuit 626 may be transmitted to an OR gate 630. At the OR gate, the first arriving hit signal amongst four hit signals may generate the output of the OR gate. Whichever hit signal (from one of the first timing pick-off circuit 622, the second timing pick-off circuit 624, the third timing pick-off circuit 628, and the fourth timing pick-off circuit 626) reaches the OR gate first may initiate the timing digitization in a time to digital converter (TDC) 632. By design, when the signal trace lengths are kept same, the largest signal among the outputs of the output arrays of 614, 616, 616, 620, may generate the hit signal first at the timing pick-off circuits 622, 624, 626, 628 and reach the OR gate 630 first. The largest signal may contain more collected SiPM signals that minimizes the effect of Compton scatter. The TDC 632 may recognize events in the form of signals reaching the TDC from the OR gate 630 and provide a digital representation of the time they occurred.

In this way, the system shown in FIGS. 1-7 provides for a detector ring including a plurality of detector blocks, each detector block including an array of scintillation crystals and an array of silicon photomultiplier (SiPM) devices, the array of SiPM devices divided into two or more regions with each region including at least one SiPM device, and two or more timing pick-off circuits with each of the two or more timing pick-off circuits coupled to one of the two or more regions via a distinct output array. The two or more timing pick-off circuits may transmit individual signals from the two or more regions of the array to a single logic circuit. The two or more regions may include at least one common SiPM device, the at least one common SiPM coupled to at least two timing pick-off circuits.

FIG. 8 shows a high-level flow chart illustrating an example method 800 for processing signal from a silicon photomultiplier (SiPM) array. Method 800 may be carried out using the systems and components described herein above with regard to FIGS. 1-7. For example, it may be accomplished by a combination of an analog ASIC and a TDC or a hybrid ASIC. However, it should be understood that the method may be carried out using different systems and components without departing from the scope of the disclosure.

At 802, an analog signal is generated at each SiPM (such as SiPM 404 in FIG. 4) in a detector block corresponding to a scintillation event. A detector block may include a plurality of SiPMs arranged in an array. The SiPMs within an array may be divided into two or more regions. When a photon collides with a detector crystal on a detector ring, it produces a scintillation event on the crystal. Each SiPM constituting the crystal produces an analog signal when a scintillation event occurs.

At 804, signals from each SiPM in a region (such as first region 406 in FIG. 4) may be transmitted to a dedicated output channel (such as output channel 411 in FIG. 4). The output channel may be part of an output array (such as output array 410 in FIG. 4). The output array may include a plurality of output channels with each output channel corresponding to a specific SiPM within a region. Each region within a SiPM array may correspond to an output array. As an example, a region with eight SiPMs may correspond to an output array with eight output channels.

At 806, signals from each output channel within an output array may be summed. In this way, signals from all SiPMs within a region may be summed in an output array. At 808, the summed signal from an output array may be transmitted to a timing pick-off circuit. Each output array may correspond to a specific timing pick-off circuit. In this way, signal from each region in the SiPM array is summed and transmitted to a corresponding timing pick-off circuit.

At 810, at the timing pick-off circuit, the signal is transmitted through an amplifier, a capacitor, and a comparator. At the timing pick-off circuit, the signal is compared to a threshold signal and if the signal is higher than the threshold signal, a square pulse may be generated. The square pulse may be termed as a hit signal generated from the timing pick-off circuit. Hit signals may be generated at each timing pick-off circuit.

At 812, hit signals from each timing pick-off circuit may be transmitted to an OR gate (such as OR gate 418 in FIG. 4). At 814, whichever hit signal reaches the OR gate first may be transmitted to a time to digital converter (such as TDC 420 in FIG. 4). At 816, the TDC may provide a digital representation of the time of occurrence of the scintillation event. For example, a TDC might output the time of arrival for each incoming signal.

At 818, the digital signal generated at the TDC may be transmitted to a data acquisition processor (such as data acquisition processor 48 in FIG. 2). The data acquired by the data acquisition processor is reconstructed using an image reconstruction processor.

In this way, first signals generated at silicon photomultiplier (SiPM) devices included in a first region of a SiPM device array may be transmitted to a first timing pick-off circuit via a first output array, a first hit signal corresponding to the first region of the SiPM device array may be generated at the first timing pick-off circuit, second signals generated at SiPM devices included in a second region of a SiPM device array may be transmitted to a second timing pick-off circuit via a second output array, a second hit signal corresponding to the second region of the SiPM device array may be generated at the second timing pick-off circuit, and one of the first hit signal and the second hit signal may be transmitted via a logic circuit coupled to each of the first timing pick-off circuit and the second timing pick-off circuit to reduce dark counts.

In this way, with even an increased number of SiPMs in a detector block, the CTR may be improved. The technical effect of dividing a SiPM array into two or more regions with signal from each region used as an input signal for a single timing pick-off circuit is that the detrimental effects of dark counts may be reduced. By summing dark counts from a fewer number of SiPMs, signal quality may be improved. By dividing the SiPM array into overlapping regions and adding one or more further timing pick-off circuits, SiPM signal may be duplicated in the overlap region and the CTR of the inter-region Compton scatter signals may be improved.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. An imaging system, comprising:
one or more detector blocks, each detector block including an array of silicon photomultiplier (SiPM) devices divided into a plurality of regions, with the SiPM devices in the plurality of regions transmitting signals to a plurality of distinct timing pick-off circuits, wherein a first number of SiPM devices are included only in a first region of the plurality of regions, a second number of SiPM devices are included only in a second region of the plurality of regions, and a third number of SiPM devices are included in two or more of the first region, the second region, and a third region of the plurality of regions.

2. The system of claim 1, wherein the one or more detector blocks constitute a detector ring assembly of the imaging system.

3. The system of claim 1, wherein each of the plurality of regions in the array of SiPM devices include at least one SiPM device.

4. The system of claim 3, wherein the at least one SiPM device is included in one of the plurality of regions, one or more of the plurality of regions being mutually exclusive.

5. The system of claim 3, wherein the at least one SiPM device is included in two of the plurality of regions, at least two of the two of the plurality of regions overlapping each other.

6. The system of claim 1, wherein each region of the plurality of regions transmits signal to one of the plurality of distinct timing pick-off circuits via an output array.

7. The system of claim 6, wherein the output array includes a number of output channels.

8. The system of claim 7, wherein the number of output channels in the output array is equal to a number of SiPM devices in a region coupled to the output array, with each SiPM device mapped to an output channel in the output array.

9. The system of claim 7, wherein transmitting the signal to the one of the plurality of distinct timing pick-off circuits via the output array includes each output channel receiving an analog signal from a SiPM device and the output array summing each analog signal from each output channel in the output array to generate an input signal for a timing pick-off circuit coupled to the output array, the analog signal generated upon collision of a photon with the SiPM device.

10. The system of claim 9, wherein each timing pick-off circuit of the plurality of distinct timing pick-off circuits includes a summing amplifier, a capacitor, and a comparator connected in series, each timing pick-off circuit comparing the input signal to a threshold signal and, in response to the input signal being higher than the threshold signal, generating a square pulse signal.

11. The system of claim 9, wherein each timing pick-off circuit output of the plurality of distinct timing pick-off circuits is coupled to a logic circuit.

12. The system of claim 11, wherein the logic circuit receives square pulse signals from the plurality of distinct timing pick-off circuits and transmits a square pulse signal reaching the logic circuit first to a time-to-digital converter.

13. A method for an imaging system, comprising:
transmitting first signals generated at silicon photomultiplier (SiPM) devices included in a first region of a SiPM device array to a first timing pick-off circuit via a first output array;
generating a first hit signal corresponding to the first region of the SiPM device array at the first timing pick-off circuit;
transmitting second signals generated at SiPM devices included in a second region of the SiPM device array to a second timing pick-off circuit via a second output array;
generating a second hit signal corresponding to the second region of the SiPM device array at the second timing pick-off circuits;
transmitting third signals generated at SiPM devices included in a third region of the SiPM device array to a third timing pick-off circuit via a third output array, the SiPM devices included in the third region are also included in one or more of the first region and the second region;
generating a third hit signal corresponding to the third region of the SiPM device array at the third timing pick-off circuit; and
transmitting one of the first hit signal the second hit signal, and the third hit signal via a logic circuit coupled to each of the first timing pick-off circuit and the second timing pick-off circuit to reduce dark counts.

14. The method of claim 13, wherein the first signals generated at the SiPM devices in the first region are summed at the first output array and a first input signal from the first output array is transmitted to the first timing pick-off circuit, the second signals generated at the SiPM devices in the second region are summed at the second output array and a second input signal from the second output array is transmitted to the second timing pick-off circuit, and the third signals generated at the SiPM devices in the third region are summed at the third output array and a third input signal from the third output array is transmitted to the third timing pick-off circuit.

15. The method of claim 13, wherein the first region of the SiPM device array includes a first number of SiPM devices, with each SiPM device of the first number of SiPM devices coupled to a distinct output channel in the first output array, wherein the second region of the SiPM device array includes a second number of SiPM devices, with each SiPM device of the second number of SiPM devices coupled to a distinct output channel in the second output array, and wherein the third region of the SiPM device array includes a third number of SiPM devices, with each SiPM device of the third number of SiPM devices coupled to a distinct output channel in the third output array.

16. The method of claim 13, wherein the first region of the SiPM device array overlaps with the second region of the SiPM device array, with one or more SiPM devices shared between the first region and the second region.

17. The method of claim 13, wherein the SiPM device array constitutes a single detector block in a detector ring assembly of the imaging system.

18. An imaging system, comprising:
a detector ring including a plurality of detector blocks; each detector block in the plurality of detector blocks including an array of silicon photomultiplier (SiPM) devices, the array of SiPM devices divided into a plurality of regions, with each region including at least one SiPM device; wherein a first number of SiPM devices are included only in a first region of the plurality of regions, a second number of SiPM devices are included only in a second region of the plurality of regions, and a third number of SiPM devices are included in each of a third region of the plurality of regions and one of the first region and the second region; and
two or more timing pick-off circuits, each of the two or more timing pick-off circuits coupled to one of the plurality of regions via a distinct output array.

19. The system of claim 18, wherein the two or more timing pick-off circuits transmit individual signals from the plurality of regions of the array to a single logic circuit.

20. The system of claim 18, wherein the plurality of regions include at least one common SiPM device, the at least one common SiPM coupled to at least two timing pick-off circuits.

* * * * *